United States Patent [19]

Olson et al.

[11] 4,310,465

[45] Jan. 12, 1982

[54] SYNTHESIS OF VITAMIN E AND QUINONE INTERMEDIATES

[75] Inventors: Gary L. Olson, Westfield; Gabriel Saucy, Essex Fells, both of N.J.

[73] Assignee: Hoffmann-La Roche Inc., Nutley, N.J.

[21] Appl. No.: 104,488

[22] Filed: Dec. 17, 1979

Related U.S. Application Data

[60] Continuation of Ser. No. 941,445, Sep. 11, 1978, abandoned, which is a division of Ser. No. 797,713, May 17, 1977, Pat. No. 4,127,608.

[51] Int. Cl.³ .................... C07C 46/06; C07C 50/28
[52] U.S. Cl. ................ 260/396 R; 568/662; 568/763; 260/345.5; 568/772; 260/345.8 R; 260/345.9 R; 260/348.17; 260/348.25; 260/348.29; 260/456 P; 260/456 R; 556/436; 556/441; 556/449; 560/57; 560/66; 560/67; 560/106; 560/112; 560/228; 560/230; 560/240; 560/254; 560/264; 564/291; 564/295; 568/308; 568/315; 568/325; 568/386; 568/412; 568/413; 568/593; 568/607; 568/660
[58] Field of Search ............ 260/396 R, 345.9 R

[56] References Cited

U.S. PATENT DOCUMENTS 2,782,210  2/1957  Teuber ........................ 260/396 R
3,564,025  2/1971  Folkers et al. .............. 260/396 R
4,113,740  9/1978  Cohen et al. ................ 260/396 R Primary Examiner—Vivian Garner
Attorney, Agent, or Firm—Jon S. Saxe; George M. Gould; William H. Epstein

[57] ABSTRACT

A synthesis of Vitamin E has the condensation of 2,4-pentanediene and 1,2-epoxy-2,6,10,14-tetramethylpentadecane including intermediates in this synthesis which uses base catalyzed condensations of aliphatic compounds to construct the Vitamin E molecule from aliphatic precursors.

4 Claims, No Drawings

SYNTHESIS OF VITAMIN E AND QUINONE INTERMEDIATES

This is a continuation of application Ser. No. 941,445 filed Sept. 11, 1978, abandoned, which in turn is a division application of Ser. No. 797,713, filed May 17, 1977, U.S. Pat. No. 4,127,608.

SUMMARY OF INVENTION

In accordance with this invention, there is provided a method for synthesizing compounds of the formula:

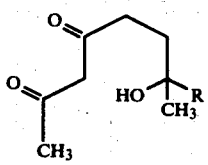

wherein R is

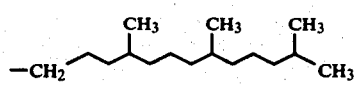

or $-CH_2-(CH_2)_n-OR_1$;

n is an integer of from 0 to 1 and $R_1$ taken together with its attached oxygen atom forms an ester group removable by hydrolysis or an ether group removable by hydrogenolysis or acid catalyzed cleavage by condensing a compound of the formula

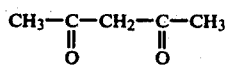

with a compound of the formula:

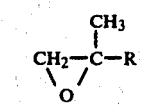

where R is as above.

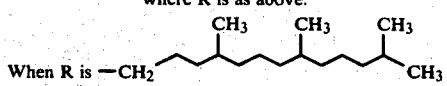

the compound of formula I is converted to Vitamin E which has the following formula:

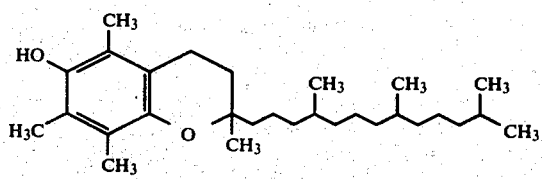

On the other hand, when R is $-CH_2-(CH_2)_n-OR_1$, the compound of formula I can be converted to produce the compound of the formula:

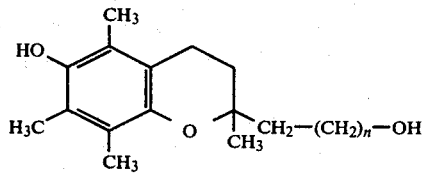

wherein n is as above which are all well-known intermediates in the synthesis of Vitamin E [see Mayer et al. Helv. Chem. Acta., 46, 650 (1963) and Scott et al., Helv. Chem Acta, 59, 290 (1976)].

DETAILED DESCRIPTION

As used throughout this application, the term "lower alkyl" comprehends both straight and branched chain saturated hydrocarbon groups containing from 1 to 7 carbon atoms such as methyl, ethyl, propyl, isopropyl, etc. As used throughout this application, the term "halogen" includes all four halogens, such as bromine, chlorine, fluorine and iodine. The term "alkali metal" includes sodium, potassium, lithium, etc.

The term "lower alkoxy" as used throughout the specfication denotes lower alkoxy groups containing from 1 to 7 carbon atoms such as methoxy, ethoxy, propoxy, isopropoxy, etc. The term "lower alkanoyl" as used throughout this specification denotes lower alkanoyl groups containing from 2 to 6 carbon atoms such as acetyl or propionyl. As used herein the term "aryl" designates mononuclear aromatic hydrocarbon groups such as phenyl, which can be unsubstituted or substituted in one or more positions with a lower alkylenedioxy, a halogen, a nitro, a lower alkyl or a lower alkoxy substituent, and polynuclear aryl groups such as naphthyl, anthryl, phenanthryl, azulyl, etc., which can be unsubstituted or substituted with one or more of the aforementioned groups. The preferred aryl groups are the unsubstituted mononuclear aryl groups, particularly phenyl. The term "aryl lower alkyl" comprehends groups wherein aryl and lower alkyl are as defined above, particularly benzyl. The term "aroic acid" comprehends acids wherein the aryl group is defined as above. The preferred aroic acid is benzoic acid.

As used herein the term "alcohol protecting group" comprehends any conventional organic alcohol protecting group such as those listed in McOmie, "Protective Groups in Organic Chemistry," Chapter 3, Plenum Press, New York, 1973; Harrison and Harrison, "Compendium of Organic Synthetic Methods," Vols. I, II, Sect. 45-A, John Wiley and Sons, New York, 1971 and 1974; "Annual Reports in Organic Synthesis", 1970-1975, Sect. V-A, Academic Press, New York, 1971-1976.

Exemplary protecting groups are esters removable by hydrolysis such as acetates, benzoates, trihaloacetates, methanesulfonates and p-toluenesulfonates; ethers removable by hydrolysis such as tetrahydropyranyl, t-butyl, methoxymethyl, 2-ethoxyethyl; trialkylsilyl ethers such as trimethylsilyl and t-butyldimethylsilyl; ethers removable by hydrogenolysis such as benzyl, alkyl or benzhydryl ethers.

The preferred ethers which are removed by acid hydrolysis are tetrahydropyranyl, 2-ethoxyethyl and t-butyl.

The preferred ethers which are removed by hydrogenolysis are benzyl and substituted benzyl.

The preferred esters which are removed by acid or base hydrolysis are acetates, formates and benzoates.

In accordance with this invention, the compound of formula III is prepared by reacting a compound of the formula

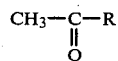   X wherein R is as above
with a conventional methylenation agent such as dimethylsulfonium methylide or dimethyloxosulfonium methylide as disclosed by Corey et al. in J. Amer. Chem. Soc., 84, 3782 (1962); Ibid., 87, 1353 (1965), Ibid., 84, 867 (1962).

In accordance with a preferred embodiment of this invention, the sulfonium methylide is formed by treating trimethylsulfonium chloride with sodamide in liquid ammonia. After formation of dimethylsulfonium methylide, the compound of formula X is added to the same reaction mixture in which the dimethylsulfonium methylide was formed. Temperatures are utilized in this reaction to maintain the ammonia in a liquid state during the reaction.

Alternatively, the compound of formula X may be converted to the compound of formula III by a two-step procedure in which the compound of formula X is first treated with a methylenetriarylphosphorane such as methylenetriphenylphosphorane to form an olefin of the formula:

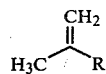   XI wherein R is as above.

The methylenetriphenylphosphorane is generated by any conventional means for example as disclosed by Wittig et al. in Org. Syn., 40, 66 (1960). For example, it is generated by treatment of a methyltriphenylphosphonium halide, e.g. methyltriphenylphosphonium bromide with a strong base, such as n-butyllithium in an inert organic solvent such as tetrahydrofuran. The methylenetriphenylphosphorane is then reacted with the compound of formula X in the same reaction mixture in which the methylenetriphenylphosphorane was formed.

The compound of formula XI is converted to the compound of formula III by oxidation with a peracid. Any conventional peracid may be used such as peracetic acid, m-chloroperbenzoic acid, monoperphthalic acid and percamphoric acid. This reaction is carried out by adding a solution of the peracid to a solution of the compound of formula XI in an inert organic solvent such as dichloromethane or acetic acid at a temperature of $-10°$ C. to room temperature.

When R, in the compound of formula XI is $-CH_2-(CH_2)_n-OR_1$ and $R_1$ is hydrogen i.e., a compound of the formula:

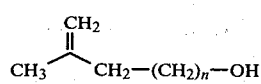   XI-A it may be converted to the compound of the formula III where R is $-CH_2-(CH_2)_n-OR_1$ and $R_1$ is hydrogen, i.e. a compound of the formula:

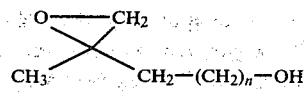   III-A by the above peracid reagents or by epoxidation using an organic hydroperoxide in the presence of vanadium or molybdenum catalyst according to the procedure of Sharpless et al., J. Amer. Chem. Soc., 95, 6136 (1973); Ibid., 96, 5354 (1974).

In order to form the compound of formula I, the dianion of the compound of formula II which has the formula:

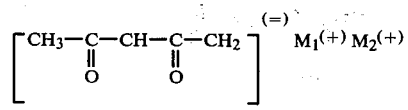   II-A wherein $M_1^+$ and $M_2^+$ are alkali metal ions
is condensed with the compound of formula III. This reaction is carried out in an anhydrous aprotric solvent. Any conventional anhydrous aprotic solvent can be utilized to carry out this condensation. Among the preferred aprotic solvents are included diethyl ether, tetrahydrofuran, hexamethylphosphoramide, etc. This condensation is carried out at a temperature of from $-10°$ C. to 50° C.

The dianion of formula II-A is prepared from the compound of formula II via the monoanion of the formula

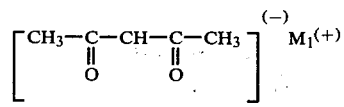   II-B wherein $M_1$ is as above.

The compound of formula II is converted to the monoanion of formula II-B by treating at a temperature of $-70°$ C. to 20° C. the compound of formula II with a base to form the monoanion of formula II-B. In forming the monoanion, it is preferred to react the compound of formula II with one equivalent of the base per equivalent of the compound of formula II. The preferred bases are sodium hydride, sodamide, lithium dialkylamides, potassium hydride, alkali metal hydroxides or alkoxides or an alkali metal. The reaction may be carried out in an inert solvent. Among the preferred solvents are alkanols such as ethanol, methanol, etc., water, diethyl ether, tetrahydrofuran, dimethylformamide or hexamethylphosphoramide. If a solvent other than an aprotic solvent is utilized, it must be replaced by an aprotic anhydrous solvent in order to carry out the next step of converting the monanion of formula II-B to the dianion of formula II-A. This non-aprotic solvent can be removed by evaporation to obtain the monoanion, there is added an aprotic anhydrous solvent medium to carry out the conversion of a compound of formula II-B to the dianion of formula II-A.

The conversion of the monoanion of formula II-B to the dianion of formula II-A is carried out by treating the monoanion of formula II-B with a strong base in an anhydrous aprotic solvent at a temperature of from −70° C. to 20° C. Any conventional solvent can be utilized in carrying out this reaction. Among the strong bases which are suitable for carrying out this reaction are included alkyl lithium, alkali metal dialkylamides or sodamide. Among the preferred strong bases are included butyllithium, methyllithium, lithium diisopropylamide. The formation of the dianion of formula II-A is expediently carried out by reacting the monoanion of formula II-B with one equivalent of base per equivalent of monoanion. The dianion of formula II-B can be isolated, if desired, by low temperature evaporation of the solvent. However, since the reaction medium in which the dianion is formed can be utilized to react this dianion in the next step with the compound of formula III to form the compound of formula I, there is no necessity to isolate the dianion of formula II-A.

A preferred method for forming the dianion of the compound of formula III is by utilizing the procedure of Weiler, J. Amer. Chem. Soc., 92, 6702 (1970) through treatment of the compound of formula III with one equivalent of sodium hydride in tetrahydrofuran at 0° C. and then with one equivalent of butyllithium at 0° C. in the same solvent.

The compound of formula I is next converted to a compound of the formula

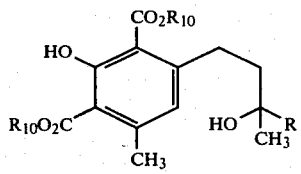
XV wherein R is as above and $R_{10}$ is lower alkyl.

The compound of formula I is converted to the compound of formula XV by reacting the compound of formula I with a di(lower alkyl)acetone-1,3-dicarboxylate such as dimethyl acetone-1,3-dicarboxylate in the presence of an alkali metal lower alkoxide in a lower alkanol solvent. Any conventional lower alkanol solvent such as methanol, ethanol, isopropanol, etc., can be utilized. Alternatively, the reaction may be carried out with an alkali metal salt of the di(lower alkyl)acetone-1,3-dicarboxylate in an inert organic solvent such as benzene, tetrahydrofuran, diethyl ether, or dimethylformamide. In carrying out these reactions, temperature and pressure are not critical and this reaction can be carried out at room temperature and atmospheric pressure. If desired, higher or lower pressures and/or temperatures can be utilized.

The compound of formula XV is next converted to a compound of the formula

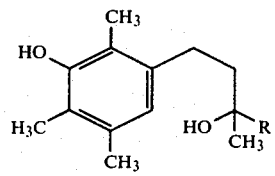
XVI wherein R is as above
by treatment with an aluminum hydride reducing agent.

The compound of formula XV is converted to the compound of formula XVI by treating the compound of formula XV with an aluminum hydride reducing agent at a temperature of from 120° C. to 180° C. In carrying out this reaction, any conventional aluminum hydride reducing agent, which does not decompose at temperatures above 120° C., preferably from 120° C. to 180° C., can be utilized to carry out this reaction. Among the preferred aluminum hydride reducing agents are sodium dihydrobis[2-methoxyethoxy]aluminate and di(-lower alkyl) aluminum hydrides such as diisobutyl aluminum hydride. In carrying out this reaction, any inert organic solvent can be utilized. Among the preferred inert organic solvents are the inert organic solvents boiling above 120° C. at atmospheric pressure such as diglyme, xylene, etc. If desired, inert organic solvents which are lower boiling can be utilized at temperatures of 120°–180° C., if the reaction is carried out under pressure.

In the next step of this process, the compound of formula XVI is converted to a compound of the formula:

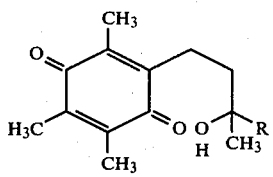
XVII where R is as above
by reacting the compound of formula XVI with an oxidizing agent described hereinafter.

Where R in the compound of formula XV is —CH$_2$—(CH$_2$)$_n$—OR$_1$, a compound of the formula:

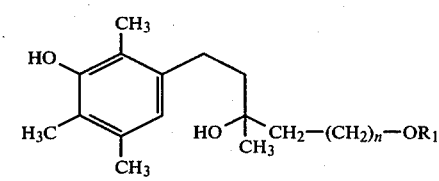
XVI-A wherein n and $R_1$ are as above
is formed which is thereafter converted to a compound of the formula:

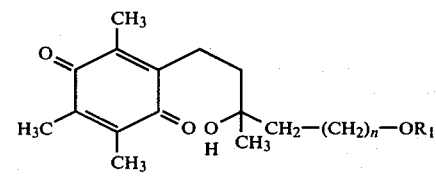
XVII-A wherein $R_1$ and n are as above
by reacting the compound of formula XVI-A with an oxidizing agent as described hereinafter.

The compound of formula XVI-A is converted to the compound of formula XVII-A by oxidation with a nitrosodisulfonate salt of the formula

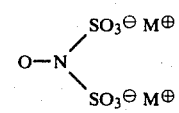
XX wherein M is an alkali metal.

Among the preferred nitrosodisulfonate salts are included Fremy's salt. In carrying out this reaction, any of the conditions conventional in oxidizing with Fremy's salt as well as other nitrosodisulfonates can be utilized. Generally, this reaction is carried out in an aqueous medium. In carrying out this oxidation, temperature and pressure are not critical and this reaction can be carried out at room temperature and atmospheric pressure. On the other hand, elevated or reduced temperatures can be utilized.

On the other hand, where R in the compound of formula XVI is,

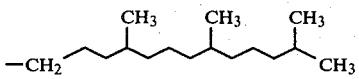

i.e., a compound of the formula

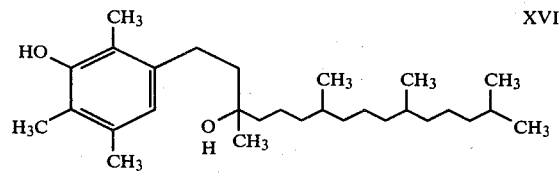

XVI-B

There is no reaction between the oxidizing agent of formula XX and the compound of formula

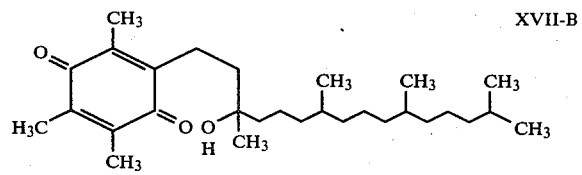

XVII-B is not formed.

In accordance with this invention, we have discovered a new organic-soluble oxidizing agent which will convert the compound of formula XVI-B to the compound of formula XVII-B. This oxidizing agent has the formula

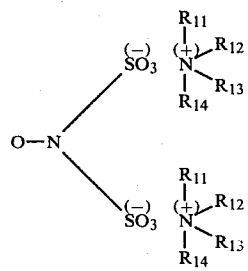

XXI wherein $R_{11}$, $R_{12}$ and $R_{13}$ are alkyl containing from 1 to 20 carbon atoms and $R_{14}$ is alkyl containing 8 to 20 carbon atoms.

The oxidizing agent of formula XXI can also oxidize the compound of formula XVI-A to the compound of formula XVII-A and is generally effective in oxidizing phenols usually oxidized with Fremy's salt, e.g., durophenol.

In the compound of formula XXI, $R_{11}$, $R_{12}$ and $R_{13}$ can be any straight or branched chain alkyl group containing from 1 to 20 carbon atoms such as methyl, n-octyl, isopropyl, ethyl, n-decyl 2,4,6-trimethyldodecyl, n-octadecyl, etc. Also, $R_{14}$ can be any straight or branched chain alkyl group containing from 8 to 20 carbon atoms such as n-decyl, n-octyl, 2,4,6-trimethyldodecyl, n-octadecyl, etc. Among the preferred compounds of formula XXI are compounds such as tri(n-octyl)mono methyl ammonium nitrosodisulfonate and tri(n-decyl)mono methylammonium nitrosodisulfonate.

The compound of formula XXI is formed by reacting the compound of formula XX with a quaternary ammonium salt of the formula

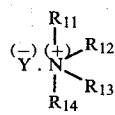

XXII wherein $R_{11}$, $R_{12}$, $R_{13}$ and $R_{14}$ are as above and $Y^{\ominus}$ is a halide or $HSO_4^{\ominus}$ ion.

This reaction is carried out in a two phase system consisting of an aqueous solution or suspension of the salt of formula XX and an inert organic solvent such as toluene, benzene, xylene, etc. In carrying out this reaction, temperature and pressure are not critical and this reaction can be carried out at room temperature or atmospheric pressure. The compound of formula XXI is formed in the organic layer. On the other hand, higher or lower temperatures can be utilized. Generally, this reaction is carried out at a temperature of from 0° C. to 50° C. The salt of formula XXI can be isolated from the reaction medium by separating the aqueous layer and evaporating the organic solvent. However, since the salt of formula XXI can be utilized to oxidize the compound of formula XVI to a compound of formula XVII in the solvent medium, one need not isolate the salt of formula XXI from the reaction medium but may oxidize the compound of formula XVI to the compound of formula XVII directly in the solvent medium.

In addition, the compound of formula XXI need not be formed in stoichiometric amount to the phenol of formula XVI-B since the oxidation may be run by adding a catalytic amount of the quaternary ammonium salt of formula XXII to a two-phase water-organic solvent medium containing a stoichiometric amount of the compound of the formula XX. The oxidation can be run with 0.01–5.0 equivalents of the ammonium salt of formula XXII.

In carrying out this oxidation reaction, temperature and pressure are not critical and this reaction can be carried out at room temperature and atmospheric pressure. On the other hand, elevated or reduced temperatures can be utilized. Generally, it is preferred to utilize temperatures of from 0° C. to 50° C.

The compound of formula XVII-B can be converted to Vitamin E by reaction with sulfuric acid in methanol such as described by Mayer et al. *Helv. Chim. Acta*, 50, 1168 (1967) or reductive cyclization with butyl mercaptan such as disclosed by Oxman and Cohen, *Biochem. Biophys. Acta*, 173, 412 (1966). In the same manner, the compound of formula XVII-A can be converted to a compound of the formula:

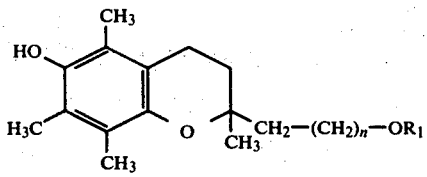

V-A wherein R₁ is as above.

Where R₁ forms an ester, any conventional method of ester hydrolysis can be utilized to convert the compound of formula V-A to a compound of formula V. Wherein R₁ forms an ether group removable by hydrogenolysis, any conventional method of hydrogenolysis can be utilized to effect this conversion. On the other hand, where R₁ forms an ether group removable by acid catalyzed cleavage, any conventional method of acid catalyzed cleavage can be utilized to effect this conversion.

The following examples are illustrative but not limitative of the invention. In the examples, all temperatures are in degrees centigrade. The ether utilized in the following examples is diethyl ether.

EXAMPLE 1

1,2-Epoxy-2,6,10,14-tetramethylpentadecane

To a solution of sodamide in 120 ml of liquid ammonia under reflux (prepared from 9.12 g (0.40 mol) of sodium) was added a solution of 80.0 g (0.29 mol) of hexadhydrofarnesylacetone in 300 ml of diethyl ether while maintaining a temperature of −33° with external cooling in a Dry Ice-isopropanol bath. After 15 min 45 g (0.37 mol) of trimethylsulfonium chloride was added rapidly. After the addition, the Dry Ice condenser was removed and the ammonia was allowed to evaporate while stirring overnight. The mixture was then cooled in an ice bath and 16.2 g of ammonium chloride was added. The mixture was stirred 30 min at room temperature, was filtered through Celite and washed twice with water. The ether solution was washed with brine, was dried over anhydrous magnesium sulfate and was concentrated on a rotary evaporator to give 82.18 g of crude epoxide as an oil. The crude oil (80.93 g) was distilled rapidly through a short-path distillation head to give 75.5 g of 1,2-epoxy-2,6,10,14-tetramethylpentadecane, bp 0.08 mmHg=108°–110°.

EXAMPLE 2

7-Hydroxy-7,11,15,19-tetramethyleicosane-2,4-dione

To a suspension of sodium hydride (30.0 g of 57% by weight dispersion, 0.72 mol, washed free of oil) in tetrahydrofuran (500 ml) at 0° was added dropwise over 30 min a solution of 2,4-pentanedione (71 g, 0.71 mol) in 150 ml of tetrahydrofuran to form the monosodium salt of 2,4-pentanedione in tetrahydrofuran. After stirring the tetrahydrofuran solution containing the salt for 20 min. at 0°, butyllithium (260 ml of 2.5 M solution in hexane, 0.65 mol) was added over 30 min at 0°–5° to form the sodiolithium salt of 2,4-pentanedione and the solution containing this sodiolithium salt was stirred 20 min. at 0°–5°. The 1,2-epoxy-2,6,10,14-tetramethylpentadecane (40 g, 0.142 mol) in 50 mol of tetrahydrofuran was then added in one portion and the solution was stirred for 17.5 hr. at room temperature. The solution was cooled to 0° and was poured into a vigorously stirred mixture of ice (2 kg) and conc. aqueous hydrochloric acid (114 ml). Then saturated aqueous ammonium chloride solution (100 ml) was added and the mixture was extracted with diethyl ether (3×750 ml). The combined extracts were washed with water and brine and were dried over anhydrous magnesium sulfate and concentrated on a rotary evaporator and then at 30°–35°/0.3 mmHg for 2.5 hr to give 73.50 g of crude hydroxydiketone 7-hydroxy-7,11,15,19-tetramethyleicosane-2,4-dione as an oil. An 0.360 g sample was purified by preparative thin layer chromatograph to give 0.20 g of 7-hydroxy-7,11,15,19-tetramethyleicosane-2,4-dione as a light yellow oil.

EXAMPLE 3

Dimethyl 2-hydroxy-4-methyl-6-(3-hydroxy-3,7,11,15-tetramethylhexadecanyl)-benzene-1,3-dicarboxylate To a solution of 7-hydroxy-7,11,15,19-tetramethyleicosane-2,4-dione (72.5 g) and dimethyl acetonedicarboxylate (29.6 g) in methanol (190 ml) at 0° was added a solution of sodium methoxide in methanol (from 2.44 g of sodium and 90 ml of methanol). The solution was stirred at room temperature for 44 hr and was concentrated on a rotary evaporator to remove approx. 100 ml of methanol. The residual solution was poured onto ice (500 g) and 20% (v/v) aqueous hydrochloric acid (45 ml). The mixture was extracted with ether (3×300 ml) and the combined extracts were washed with brine and dried over anhydrous sodium sulfate and were concentrated on a rotary evaporator to give 91.65 g of crude dimethyl 2-hydroxy-4-methyl-6-(3-hydroxy-3,7,11,15-tetramethyl-hexadecanyl)-benzene-1,3-dicarboxylate as an orange oil. A 90.2 g portion of the oil was dissolved in ether (400 ml) and was washed with 20% by weight aqueous potassium carbonate (to remove the unreacted dimethyl acetonedicarboxylate), brine and was dried over anhydrous sodium sulfate. The solution was concentrated on a rotary evaporator to give 83.13 g of partially purified diester dimethyl 2-hydroxy-4-methyl-6-(3-hydroxy-3,7,11,15-tetramethyl-hexadecanyl)-benzene-1,3-dicarboxylate. The total material was chromatographed on 2.45 kg of silica gel eluting with 20–30% by volume ether in hexane to give 30.83 g of dimethyl 2-hydroxy-4-methyl-6-(3-hydroxy-3,7,11,15-tetramethyl-hexadecanyl)-benzene-1,3-dicarboxylate as a colorless oil.

EXAMPLE 4

2,3,6-Trimethyl-5-(3-hydroxy-3,7,11,15-tetramethylhexadecanyl)-phenol

To a solution of the dimethyl 2-hydroxy-4-methyl-6-(3-hydroxy-3,7,11,15-tetramethyl-hexadecanyl)-benzene-1,3-dicarboxylate (5.17 g) in xylene (25 ml) at 10° was added sodium dihydrobis(2-methoxyethoxy)aluminate (20 ml of a 70% by weight solution in benzene) over 20 min with occasional cooling to keep the temperature at 10°. After 10 min the solution was heated to reflux for 1.5 hr, cooled to 10° and was poured cautiously into cold 20% by weight aqueous sulfuric acid (200 ml). The mixture was extracted with ether (3×100 ml) and the combined extracts were washed with aqueous sodium bicarbonate and brine and dried (Na₂SO₄) and concentrated on a rotary evaporator to give 4.29 g of crude 2,3,6-trimethyl-5-(3-hydroxy-3,7,11,15-tetramethylhexadecanyl)-phenol as a light yellow oil. Chromatography on silica gel eluting with ether in petroleum ether gave 3.19 g of pure 2,3,6-trimethyl-5-(3-hydroxy-3,7,11,15-tetramethylhexadecanyl)-phenol.

EXAMPLE 5

To a slurry of Fremy's salt (di-potassium nitrosodisulfonate) in sodium carbonate (1.6 g) was added 10 ml of 15% sodium carbonate solution and a solution of 0.29 g (0.72 mmol) of tri(caprylyl)monomethylammonium chloride[1] in 4 ml of benzene. The phenol, i.e., 2,3,6-trimethyl-5-(3-hydroxy-3,7,11,15-tetramethyl-hexadecanyl)-phenol (0.3 g, 0.69 mmol) in 8 ml of benzene was added and the mixture was stirred vigorously for 2.5 hr. The mixture was poured into 5 ml of water and was extracted with 10 ml of petroleum ether. The organic phase was washed with water (2×10 ml) and the cloudy mixture was dried ($Na_2SO_4$) and concentrated on a rotary evaporator. The residual crude quinone was chromatographed on 7.0 silica gel eluting with ether-petroleum ether to give 0.321 g tocopheroquinone.

[1] A mixture of tri(n-octyl)- and tri(n-decyl)-monomethylammonium chloride.

EXAMPLE 6

A solution of Fremy's salt was prepared by dissolving 8.45 g of the sodium carbonate slurry in 52 ml of 15% sodium carbonate followed by adding 0.5 g solid sodium carbonate. The concentration of the solution was determined to be 0.175 M by measuring the absorption spectrum at 440 nm where $\epsilon = 14.5$. The solution of the Fremy's salt, the phenol, i.e, 2,3,6-trimethyl-5-(3-hydroxy-3,7,11,15-tetramethylhexadecanyl)-phenol, tri(capryl)monomethylammonium chloride, and benzene (2 ml) were added in the amounts given in the table below with the reaction being monitored by thin layer chromatography to completion. This reaction gave tocopheroquinone.

| Expt. | $ON(SO_3K)_2$, ml | | phenol, | | $(C_{10}H_{21})_3NCH_3Cl$, | | time to completion |
|---|---|---|---|---|---|---|---|
| | | (mmol) | g | (mmol) | g | (mmol) | |
| 1 | 3.07 | (0.537) | 0.1 | (0.23) | 0.02 | (0.047) | 5 hr. |
| 2 | 3.07 | (0.537) | 0.1 | (0.23) | 0.09 | (0.23) | 2–3 hr. |
| 3 | 3.07 | (0.537) | 0.1 | (0.23) | 0.18 | (0.47) | 20 min. |
| 4 | 3.07 | (0.537) | 0.1 | (0.23) | 0.37 | (0.92) | 20 min. |

EXAMPLE 7

Ten ml of a deep purple 0.154 M solution of Fremy's salt in 5% (w/v) aqueous sodium carbonate was extracted with a solution prepared from 1.25 g of tri(n-decyl)monomethylammonium chloride and 10.0 ml of benzene. The purple color rapidly was transferred to the benzene layer which was separated and dried over anhydrous potassium carbonate to give a benzene solution of bis[tri(n-decyl)monomethylammonium]nitrosodisulfonate. The solution displayed an absorption maximum in the visible spectrum at $\lambda_{max} = 552-8$ nm ($\epsilon \sim 15$).

When chloroform was used in the extraction in place of benzene, the bis[tri(n-decyl)monoethylammonium]nitrosodisulfonate was obtained in the chloroform layer and after separation and drying displayed infrared absorptions at $\lambda_{max} = 1270$ and 1026 $cm^{-1}$.

EXAMPLE 8

The benzene solution of bis[tri(n-decyl)monomethylammonium]nitrosodisulfonate prepared in Example 7 was used to oxidize 2,3,6-trimethyl-5-(3-hydroxy-3,7,11,15-tetramethylhexa-decanyl)-phenol to tocopheroquinone.

We claim:

1. A process for producing a compound of the formula

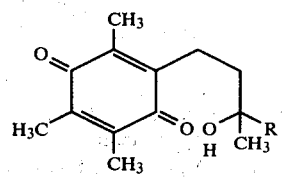

wherein R is

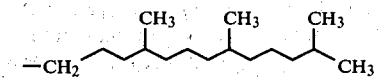

comprising oxidizing a compound of the formula

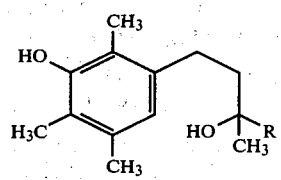

wherein R is as above
in the presence of a salt of the formula:

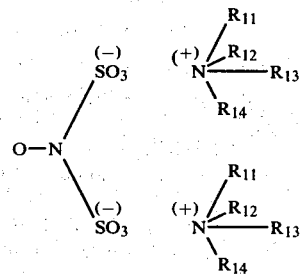

in an inert organic solvent medium
wherein $R_{11}$, $R_{12}$ and $R_{13}$ are alkyl containing from 1 to 20 carbon atoms and $R_{14}$ is alkyl containing from 8 to 20 carbon atoms.

2. The process of claim 1 wherein said salt is bis[tri(n-decyl)monomethyl ammonium]nitrosodisulfonate.

3. The process for producing a compound of the formula

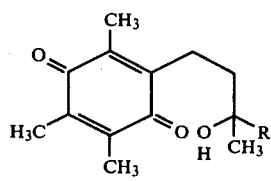

wherein R is

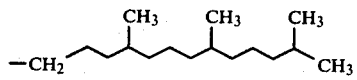

comprising oxidizing a compound of the formula

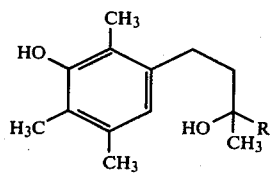

wherein R is as above
with a compound of the formula:

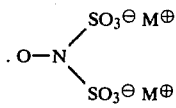

wherein M is an alkali metal;
in the presence of 0.01–5.0 equivalents of a quaternary ammonium salt of the formula:

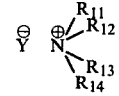

wherein $R_{11}$, $R_{12}$ and $R_{13}$ are alkyl containing from 1 to 20 carbon atoms and $R_{14}$ is alkyl containing from 8 to 20 carbon atoms and Y is halogen
in a two phase aqueous-organic solvent medium.

4. The process of claim 3 wherein said quaternary ammonium salt is tri(n-decyl)monomethyl ammonium chloride.

* * * * *